June 16, 1959 B. D. COLOMBO Plant Pat. 1,845
CAMELLIA PLANT
Filed Sept. 17, 1958 2 Sheets-Sheet 1
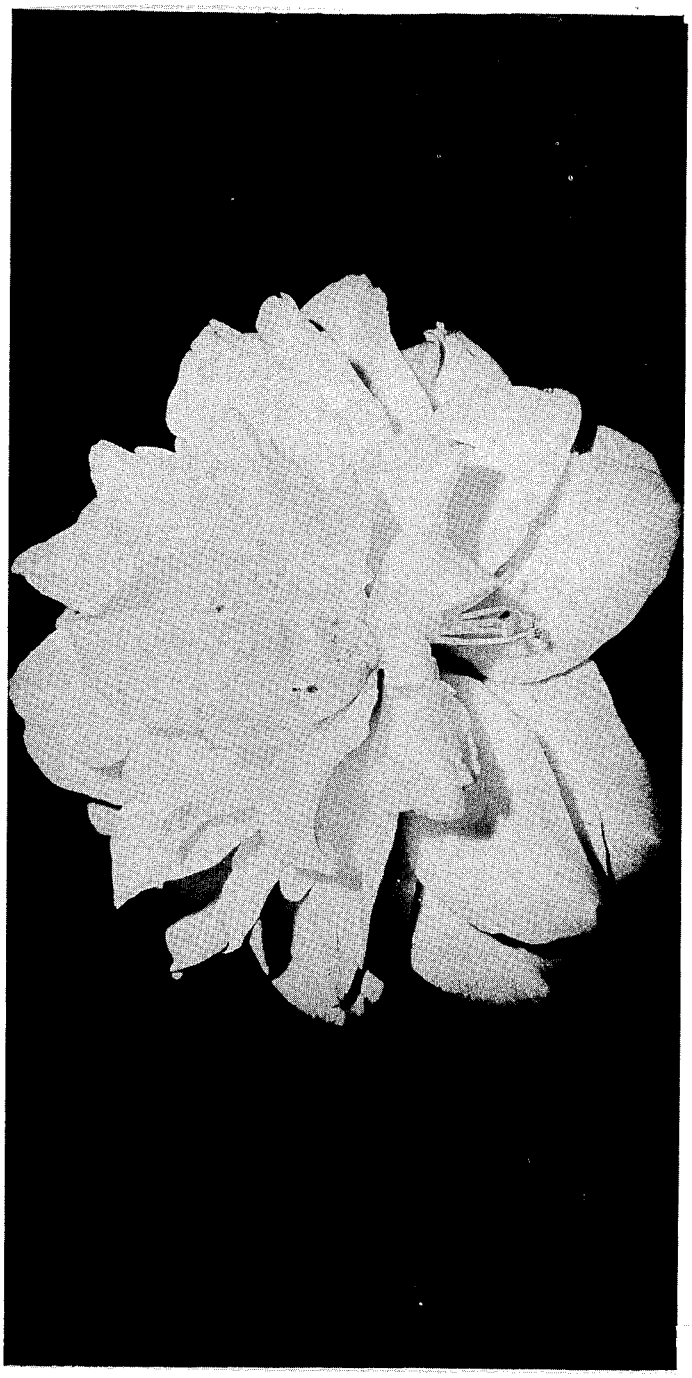
INVENTOR
Ben D. Colombo
By Townsend and Townsend
attorneys CAMELLIA PLANT
Filed Sept. 17, 1958 2 Sheets-Sheet 2
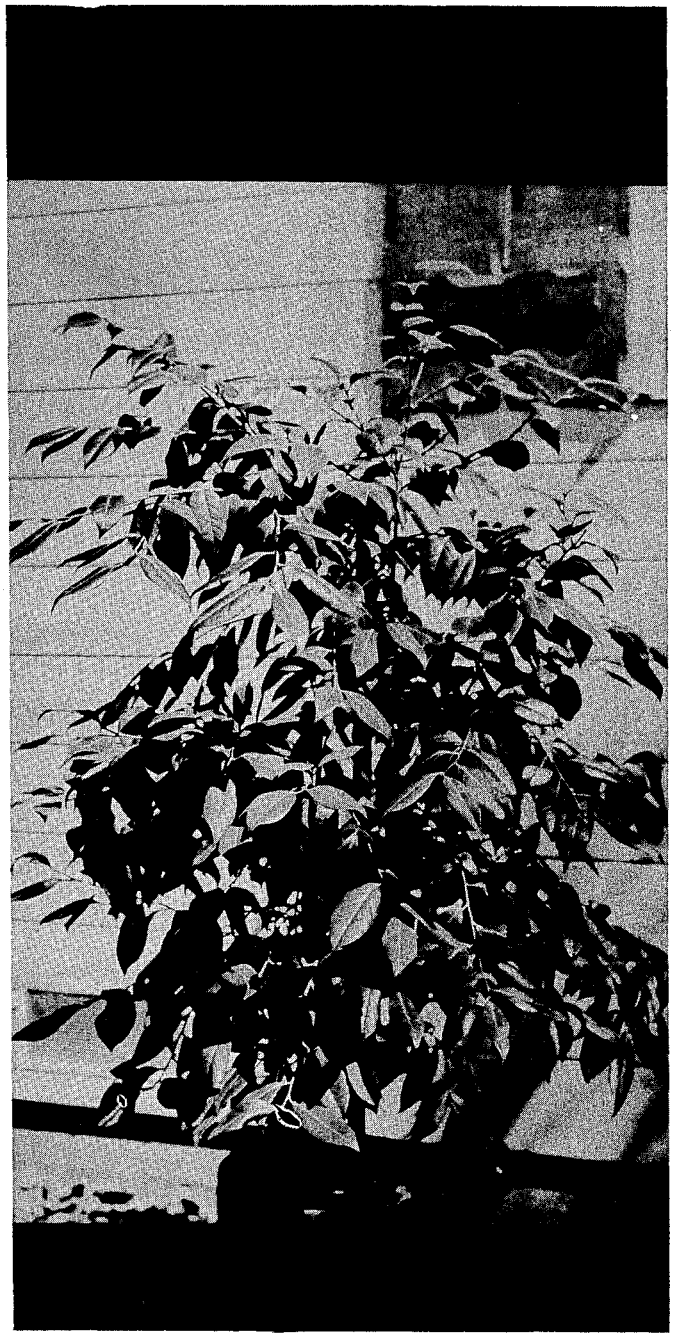
INVENTOR
Ben D. Colombo
By Townsend and Townsend
attorneys United States Patent Office Plant Pat. 1,845
Patented June 16, 1959

1,845

CAMELLIA PLANT

Ben D. Colombo, Martinez, Calif.

Application September 17, 1958, Serial No. 761,661

1 Claim. (Cl. 47—60)

The present invention relates to a new and distinct variety of camellia plant derived from the species *japonica* and which resulted from crossing a seedling of *Camellia japonica* Imura, unpatented, with an unknown male parent.

The result of my invention was a new variety of camellia having a star shaped flower and characterized by a pronounced jasmine-like fragrance. The subject of the present application is generally similar to *Camellia japonica* Imura in appearance but is distinguished from the known variety by a strong and noticeable jasmine-like scent.

Asexual reproduction of my new variety by grafting, at Martinez, California, shows the foregoing characteristics and distinctions come true to form and are established and transmitted through succeeding propagation. In addition to being definitely distinct from *Camellia japonica* Imura my new variety of camellia is definitely distinguished from all other varieties of which I am aware, none of which bear a white camellia of the characteristics hereinafter described and particularly characterized by a strong jasmine-like scent.

The accompanying drawings shows typical specimens of the flowers and foliage of my new variety. The flower shown is a fully open mature flower while the other illustration depicts a typical showing of the foliage. The color of the flower, and foliage are not points of distinction over other varieties.

The following is a detailed description of my new variety and is based upon specimens grown and observed near Martinez, California.

Parent:

*Seed parent.*—*Camellia japonica* Imura.

*Pollen parent.*—An unnamed variation.

Flowering season: January through March.

Bloom:

*Size.*—About 4¼ inches across; about 3 inches in depth.

*Borne.*—Upright on strong stock.

*Form.*—Star shape.

*Petalage.*—Profuse, semi-double with 35–40 petals while Imura has approximately 15 petals; individual petals are largely oval shaped and are definitely pointed with substantially unserrated edges except at tips of petals where a single detent or serration appears, while Imura's petals sometimes appear to be pointed; center petals lie in five tiers while Imura's petals lie in two tiers; petals are long, narrower than outer petals and tend to stand upright; texture of petals is thick, soft, velvety, satiny, and there is a difference between the texture of the inside and outside petals; lasting quality, 9–12 days on plant without shattering.

*Odor.*—Strong jasmine-like fragrance.

*Stamens.*—Anthers are medium sized substantially describing a circle around central styles and yellow in color; filaments are yellow and of medium length. The petals are interspersed among the stamens while Imura has upright central stamens free of petals.

*Seeds.*—Seeds poorly, heavy bearer.

*Plant growth habit.*—Upright, average to compact density, medium rate.

*Color.*—White

*Fragrance.*—Very strong scent of jasmine. The variety has never been outside of my nursery so at this time it is not possible to tell how it would react in other geographical locations. However, the fragrance to date has been unvarying.

Form: Brush or shrub.

Foliage:

*Size.*—Average about 4 inches long and 2 inches wide.

*Quantity.*—Average density.

*Color.*—Dark green.

*Shape.*—Oval, long and pointed leaves.

*Texture.*—Upperside glossy; underside smooth.

*Ribs and veins.*—Ordinary.

*Edge.*—Smooth.

The plant and its bloom as herein described may vary in some very slight detail due to climatic and soil conditions under which the variety may perhaps be grown.

I claim:

A new and distinct variety of camellia plant, substantially as herein shown and described, characterized particularly as to novelty by its large, semi-double, star shaped white flowers having a strong jasmine-like fragrance.

No references cited.